United States Patent [19]

Edwards

[11] Patent Number: 4,500,539

[45] Date of Patent: Feb. 19, 1985

[54] INSECTICIDAL 5-THIOCARBAMOYL-1,3,4-OXADIAZOLES

[75] Inventor: Laroy H. Edwards, Napa, Calif.

[73] Assignee: Chevron Research Company, San Francisco, Calif.

[21] Appl. No.: 514,067

[22] Filed: Jul. 15, 1983

[51] Int. Cl.³ ................ A01N 43/76; C07D 271/10
[52] U.S. Cl. .................................... 514/364; 548/144
[58] Field of Search ..................... 548/144; 424/272

[56]         References Cited
       FOREIGN PATENT DOCUMENTS 45-17189 6/1970 Japan ................................ 548/144

*Primary Examiner*—Paul M. Coughlan, Jr.
*Assistant Examiner*—Cecilia Shen

*Attorney, Agent, or Firm*—S. R. LaPaglia; T. G. DeJonghe; S. L. Biggs

[57]             ABSTRACT

Compounds of the formula:

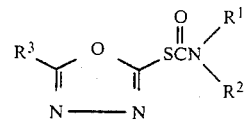

wherein $R^1$ and $R^2$ are independently lower alkyl having from 1 to 4 carbon atoms; and $R^3$ is lower alkyl having from 1 to 6 carbon atoms, lower cycloalkyl having from 3 to 6 carbon atoms optionally substituted with methyl or ethyl, lower alkoxyalkyl having up to a total of 8 carbon atoms or lower alkylthioalkyl having up to a total of 8 carbon atoms are insecticidal.

12 Claims, No Drawings

INSECTICIDAL 5-THIOCARBAMOYL-1,3,4-OXADIAZOLES

BACKGROUND OF THE INVENTION

The present invention relates to novel 5-thiocarbamoyl-1,3,4-oxadiazoles which are active as insecticides.

The cyclization of thio- and dithiocarbazic acid ester derivatives which are acylated in position 3 by the radical of a carboxyic, sulfonic, carbamic, phosphoric, thiophosphoric or thiophosphonic acid with phosgene to give compounds of the formula:

where y is O or S, Acyl is $-COC_6H_5$, $-SO_2C_6H_5$, $CO_2C_2H_5$, $CON(CH_3)_2$ or $$-\overset{X}{\underset{R''}{\overset{\|}{P}}}\diagup^{OR'},$$

is disclosed by Rufenacht in *Helvetica Chimica Acta* 56, 162–175 (1973). The compounds where Acyl is phosphoryl or thiophosphoryl $$\left\{-\overset{X}{\underset{R''}{\overset{\|}{P}}}\diagup^{OR'}\right\}$$

are disclosed as having an "insecticidal, acaricidal, and nematicidal effect"; however, the compounds where X and O are disclosed as unstable.

Rufenacht, supra, also discloses the preparation of compounds of the formulae:

The compounds of formula (B) are disclosed as "having an insecticidal and acaricidal effect" but also as "not stable enough under the conditions of practical pesticide use".

U.S. Pat. No. 3,661,926 issued to Van den Bos et al. discloses 2-oxo-3-dialkoxyphosphoro-5-alkyl (or cycloalkyl of 5 to 7 carbons)-1,3,4-oxadiazolines as insecticidal.

U.S. Pat. No. 3,523,951 issued to Rufenacht teaches derivatives of 1,3,4-thiadiazole as possessing insecticidal activity.

My commonly assigned patent application, "Insecticidal 2-Oxo-3-Dialkoxyphosphoro-5-Cyclopropyl-1,3,4-Oxadiazoline, Ser. No. 343,088, filed Jan. 27, 1982, now U.S. Pat. No. 4,426,379 discloses compounds of the formula:

wherein R is hydrogen, lower alkyl or lower alkoxy; $R^1$ and $R^2$ are independently lower alkyl; and Y is either oxygen or sulfur.

My commonly assigned U.S. patent application, "Insecticidal N-Carbamoyl-Oxadiazonin-5-Ones and Thiones" Ser. No. 514,073 filed July 15, 1983, discloses insecticidal compounds of the formula:

wherein X is oxygen or sulfur; $R^1$ and $R^2$ are independently lower alkyl having from 1 to 4 carbon atoms; and $R^3$ is lower alkyl having from 1 to 6 carbon atoms, lower cycloalkyl having from 3 to 6 carbon atoms optionally substituted with methyl or ethyl, lower alkoxyalkyl having up to a total of 8 carbon atoms or lower alkylthioalkyl having up to a total of 8 carbon atoms.

SUMMARY OF THE INVENTION

The present invention relates to insecticidal 5-thiocarbamoyl-1,3,4-oxadiazoles of the formula:

$$R^3\diagdown\underset{N\text{——}N}{\overset{\text{O}}{\underset{\|}{\text{C}}}}\diagup\overset{\text{O}}{\underset{\|}{\text{C}}}\diagdown\text{SCN}\diagup\overset{R^1}{\diagdown R^2} \quad (I)$$

wherein $R^1$ and $R^2$ are independently lower alkyl having from 1 to 4 carbon atoms; and $R^3$ is lower alkyl having from 1 to 6 carbon atoms, lower cycloalkyl having from 3 to 6 carbon atoms optionally substituted with methyl or ethyl, lower alkoxyalkyl having up to a total of 8 carbon atoms or lower alkylthioalkyl having up to a total of 8 carbon atoms.

Among other factors, the present invention is based on my finding that these compounds are surprisingly active as insecticides, and are particularly effective against common insect pests such as aphids and cockroaches.

Preferred compounds include those which have $R^3$ groups in which the carbon atom attached to the oxadiazole ring is a tertiary carbon.

DEFINITIONS

As used herein, the following terms have the following meanings, unless expressly stated to the contrary.

The term "alkyl" refers to both straight- and branched-chain alkyl groups. The term "lower alkyl" refers to both straight- and branched-chain alkyl groups having a total of from 1 to 6 carbon atoms and includes primary, secondary and tertiary alkyl groups. Typical lower alkyls include, for example, methyl, ethyl, n-propyl, isopropyl, n-butyl, isobutyl, t-butyl, n-pentyl, n-hexyl, and the like.

The term "alkylene" refers to the group $-(CH_2)_m-$ wherein m is an integer greater than zero. Typical alkylene groups include methylene, ethylene, propylene, and the like.

The term "alkoxy" refers to the group $-OR'$ wherein R' is an alkyl group. The term "lower alkoxy" refers to alkoxy groups having from 1 to 6 carbon atoms; examples include methoxy, ethoxy, n-hexoxy, n-propoxy, isopropoxy, isobutoxy, and the like.

The term "alkoxyalkyl" refers to an alkyl group substituted with an alkoxy group. The term "lower alkoxyalkyl" refers to groups having up to a total of 8 carbon atoms and includes, for example, ethoxymethyl, methoxymethyl, 2-methoxypropyl, and the like.

The term "alkylthio" refers to the group $-SR'$ wherein R' is an alkyl group. The term "lower alkylthio" refers to alkylthio groups having from 1 to 6 carbon atoms; examples include methylthio, ethylthio, n-hexylthio, n-propylthio, isopropylthio, isobutylthio, and the like.

The term "alkylthioalkyl" refers to an alkyl group substituted with an alkylthio group. The term "lower alkylthioalkyl" refers to groups having up to a total of 8 carbon atoms and includes, for example, ethylthiomethyl, methylthiomethyl, 2-methylthiopropyl, and the like.

The term "cycloalkyl" refers to cyclic alkyl groups. The term "lower cycloalkyl" refers to groups having from 3 to 6 carbon atoms in the ring, and includes cyclopropyl, cyclobutyl, cyclopentyl, and cyclohexyl.

The term "tertiary carbon" refers to the group

wherein R', R''' and R'''' are independently lower alkyl, or R'''' is an alkoxy or alkylthio group, or R''' and R'''' taken together are an alkylene group, thus forming a cycloalkyl group.

The term "oxadiazole" refers to the group

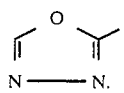

The conventional numbering system for this group is shown below:

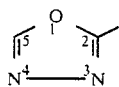

DETAILED DESCRIPTION OF THE INVENTION

The compounds of the present invention may be prepared according to the following reaction scheme:

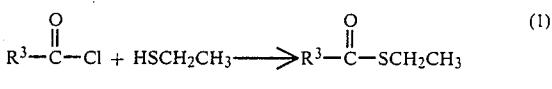

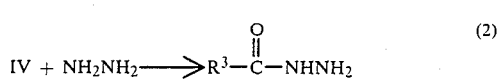

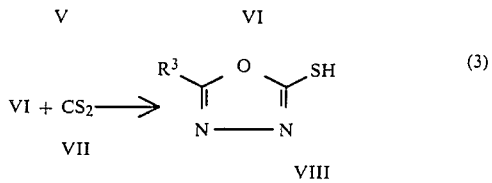

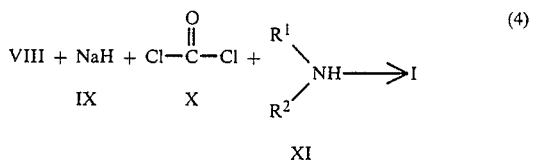

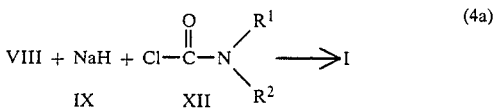

Reaction (1) is conducted by combining approximately equimolar amounts of II and III. It is preferred to add III slowly to cooled and stirred II. The reaction is conducted at a temperature from about 0° C. to about 50° C., preferably from about 0° C. to about 25° C., and is generally complete within about 3 to about 8 hours. The product, IV, is isolated by conventional procedures such as washing, extraction, drying, stripping, and the like, or alternatively, is used in Reaction (2) without further isolation and/or purification.

Reaction (2) is conducted by combining approximately equimolar amounts of IV and V in solvent. It is preferred to slowly add V to a cooled and stirred mixture of IV and water. Suitable solvents include protic solvents such as low molecular weight alcohols (methanol, ethanol, isopropyl alcohol, etc.), water and the like. Hydrazine, V, may be used either in its anhydrous form or as a hydrazine hydrate such as hydrazine monohydrate. If anhydrous hydrazine is used, it is preferred to add a small amount of water (about 5 to 10 ml) to the reaction mixture. The reaction is conducted at a temperature from about 0° C. to about 50° C., preferably from about 0° C. to about 25° C., and is generally complete within about 8 to about 12 hours. The product, VI, is isolated by conventional procedures such as washing, extraction, drying, stripping, or the like, or alternatively, may be used in Reaction (3) without further isolation and/or purification.

Reaction (3) is conducted by combining VI, VII and solvent. Although approximately equimolar amounts of VI and VII may be used, it may be preferred to use an excess of VII due to its volatility. Although the reactants may be combined in any order, it is preferred to add VII to a stirred solution of VI in solvent. The VI-solvent may be cooled for the addition of VII, since the addition is exothermic. Suitable solvents include polar organic solvents such as dimethylformamide, dimethylsulfoxide, and the like. The reaction is conducted at a temperature from about 0° C. to about 50° C., preferably about 0° C. to about 25° C., and is generally complete within about 8 to about 18 hours. The product, VIII, is isolated by conventional procedures such as washing, extraction, drying, stripping, chromatography, distillation, and the like.

Reaction (4) is conducted by first combining IX and VII in solvent; it is preferred to add IX to a cooled solution (about $-10°$ C. to about 10° C.) of VII in solvent. The resulting mixture is allowed to stir about ½ to about 1 hour to allow the reagents to react. Then X is added to the reaction system. It is preferred to cool the reaction system again prior to adding X. The reaction system is then stirred about 1 to about 2 hours to allow for reaction. Then, XI is added to the reaction system, which has been preferably cooled before adding the XI. The reaction is conducted at a temperature from about 0° C. to about 50° C., and is generally complete within about 5 to about 12 hours. For convenience, the reaction mixture may be stirred about 8 to about 12 hours between the various additions. If desired, the reaction system is cooled to about $-10°$ C. to about 20° C. before each addition, because of the exothermic nature of the additions. Suitable solvents include polar organic solvents such as dimethoxyethane, tetrahydrofuran, and the like. The product, I, is isolated by conventional procedures such as washing, extraction, drying, stripping, chromatography, distillation, and the like.

Alternatively, I may be prepared from VIII according to Reaction (4a) which uses XII in place of phosgene (X) and dialkylamine (XI). Thus, Reaction (4a) is conducted by first combining IX and VIII in solvent. It is preferred to add IX slowly to a stirred mixture of VIII in solvent which has been cooled to about $-10°$ C. to about 10° C. The resulting mixture is then stirred about 2 to about 6 hours to allow for complete reaction of the reagents, cooled as previously, and then XII is added slowly. The reaction is conducted at a temperature of about 0° C. to about 50° C., and is generally complete within 2 to about 8 hours. Suitable solvents include polar organic solvents such as dimethoxyethane, tetrahydrofuran, and the like.

UTILITY

The compounds of this invention are useful for controlling insects, particularly such insects as aphids and cockroaches. However, some insecticidal compounds of this invention may be more insecticidially active than others against particular pests.

Like most insecticidals, they are not usually applied full strength, but are generally incorporated with conventional biologically inert extenders or carriers normally employed for facilitating dispersion of active ingredients for agricultural chemical application, recognizing the accepted fact that the formulation and mode of application may effect the activity of a material. The toxicants of this invention may be applied as sprays, dusts, or granules to the insects, their environment or hosts susceptible to insect attack. They may be formulated as granules of large particle size, powdery dusts, wettable powders, emulsifiable concentrates, solutions, or as any of several other known types of formulations, depending on the desired mode of application.

Wettable powders are in the form of finely divided particles which disperse readily in water or other dispersants. These compositions normally contain from 5-80% toxicant and the rest inert material which includes dispersing agents, emulsifying agents, and wetting agents. The powder may be applied to the soil as a dry dust or preferably as a suspension in water. Typical carriers include fuller's earth, kaolin clays, silicas, and other highly absorbent, readily wet, inorganic diluents. Typical wetting, dispersing or emulsifying agents used in insecticidal formulations include, for example, the alkyl and alkylaryl sulfonates and sulfonates and their sodium salts; alkylamide sulfonates, including fatty methyl taurides; alkylaryl polyether alcohols, sulfated higher alcohols, and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1-15% by weight of the pesticidal composition.

Dusts are freely flowing admixtures of the active ingredient with finely divided solids such as talc, natural clays, keiselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersants, and may consist entirely of the toxicant with a liquid or solid emulsifying agent, or may also contain a liquid carrier such as xylene, heavy aromatic naphthas, isophorone, and other nonvolatile organic solvents. For application, these concentrates are dispersed in water or other liquid carriers, and are normally applied as a spray to the area to be treated.

Other useful formulations for insecticidal applications include simple solutions of the active ingredient in a dispersant in which it is completely soluble at the desired concentration such as acetone, alkylated naphthalenes, xylene, or other organic solvents. Granular formulations, wherein the toxicant is carried on relatively coarse particles, are of particular utility for aerial distribution or for penetration of cover-crop canopy. Baits, prepared by mixing solid or liquid concentrates of the toxicant with a suitable food such as a mixture of cornmeal and sugar, are useful formulations for control of insect pests. Pressurized sprays, typically aerosols wherein the active ingredient is dispersed in finely divided form as a result of vaporization of a low-boiling dispersant solvent carrier such as the Freons, may also be used. All of these techniques for formulating and applying the active ingredient are well known in the art.

The percentages by weight of the toxicant may vary according to the manner in which the composition is to be applied and the particular type of formulation, but in general comprise 0.1-95% of the toxicant by weight of the insecticidal composition.

The insecticidal compositions may be formulated and applied with other active ingredients, including nematocides, insecticides, fungicides, bactericides, plant-growth regulators, fertilizers, etc. In applying the chemical, an effective amount and concentration of the toxicant of this invention is, of course, employed.

The terms "insecticide" and "insect" as used herein refer to their broad and commonly understood usage rather than to those creatures which, in the strict biological sense, are classified as insects. Thus, the term "insect" is used not only to include small invertebrate animals belonging to the class "Insecta", but also to other related classes of arthropods, whose members are segmented invertebrates having more or fewer than six legs, such as spiders, mites, ticks, centipedes, worms, and the like.

A further understanding of the invention can be had in the following non-limiting Examples. Wherein, unless expressly stated to the contrary, all temperatures and temperatures ranges refer to the Centigrade system and the term "ambient" or "room temperature" refers to about 20°–25° C. The term "percent" refers to weight percent and the term "mol" or "mols" refers to gram mols. The term "equivalent" refers to a quantity of reagent equal in mols, to the mols of the preceding or succeeding reatant recited in that example in terms of finite mols or finite weight or volume. Also, unless expressly stated to the contrary, geometric isomer and racemic mixtures are used as starting materials and correspondingly, isomer mixtures are obtained as products.

EXAMPLES

Example 1

Preparation of

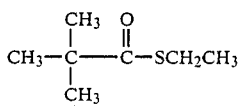

Ethyl Trimethylacetylthioate

In a three-neck flask, 50.0 g (0.411 mole) trimethylacetyl chloride were placed, then stirred and cooled in an ice-water bath. Ethanethiol, 25.5 g (0.411 mole), was then slowly added dropwise. The reaction mixture was stirred overnight and then refluxed about 8 hours, to expel hydrogen chloride gas. The reaction was stirred at room temperature over the weekend. The reaction flask was evacuated to remove any additional hydrogen chloride gas. The yield was 57.0 g. The product was used in Example 2 without further isolation.

EXAMPLE 2

Preparation of

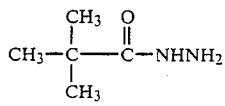

Trimethylacetyl Hydrazide

Ethyl trimethylacetylthioate (the product of Example 1), 57.0 g (0.39 mole), and ethanol were placed in a three-neck flask, then stirred and cooled with a dry ice/acetone bath. Hydrazine monohydrate, 19.5 g (0.39 mole) then was added slowly dropwise (in a very exothermic reaction). The reaction mixture was stirred overnight at room temperature, refluxed about 8 hours, and then stirred overnight at room temperature. The solvent was removed in vacuo. The above-identified product was used in Example 3 without further purification.

EXAMPLE 3

Preparation of

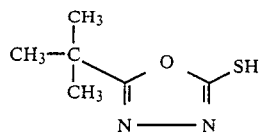

2-Mercapto-5-tert-butyl-1,3,4-Oxadiazole

A stirred mixture of 32.5 g (0.28 mole) trimethylacetyl hydrazide (the product of Example 2), in 250 ml dimethylformamide was cooled to about 0° C. in a dry ice/acetone bath. To that mixture, 21.3 g (0.28 mole) carbon disulfide was added slowly dropwise (in a moderately exothermic reaction). The reaction mixture was stirred overnight at room temperature and then refluxed about 4 hours. The reaction mixture was cooled in an ice-water bath to give an oil which was extracted with methylene chloride, dried over magnesium sulfate, stripped and chromatographed on silica gel, eluting with methylene chloride to give the above-identified product as a solid, melting point 79°–80° C.

Elemental analysis for $C_6H_{10}N_2OS$ showed: calculated %C 45.55%, %H 6.37, and %N 17.70; found %C 45.84, %H 6.47, and %N 17.84.

EXAMPLE 4

Preparation of

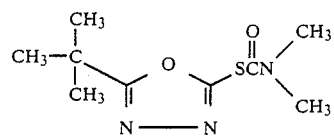

S-(N,N-Dimethylcarbamoyl)-2-Thio-5-tert-butyl-1,3,4-Oxadiazole

To a stirred mixture of 10.0 g (0.063 mole) 2-mercapto-5-tert-butyl-1,3,4-oxadiazole (the product of Example 3) in 200 ml dimethoxyethane cooled to about −10° C. in a dry ice/acetone bath, 3.0 g of 50% sodium hydride (0.063 mole) was added slowly (in a very exothermic reaction). The reaction mixture was stirred about 2 hours. The reaction mixture was cooled as before and 49.9 g of 12.5% phosgene (0.063 mole) were added (in a very exothermic reaction). The reaction mixture was stirred overnight at room temperature. The reaction mixture was cooled again as before and 5.7 g (0.126 mole) anhydrous dimethylamine was added (in an exothermic reaction). The resulting mixture was stirred overnight at room temperature. The mixture was washed with about 40 ml water, extracted with methylene chloride, dried over magnesium sulfate, and stripped to give an oil. Chromatography on silica gel, eluting with methylene chloride, gave the above-identified product as a yellow oil.

Elemental analysis for $C_9H_{15}N_3O_2S$ showed: calculated %C 47.14%, %H 6.59, and %N 18.33; found %C 47.15, %H 6.66, and %N 18.39.

EXAMPLE 5

Preparation of

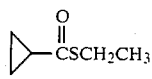

Ethyl Cyclopropane Carboxythioate

In a three-neck, 500-ml flask, 56.0 g (0.469 mole) cyclopropane carboxylic acid chloride were placed, stirred and cooled to about 10° C. with an ice-water bath. Ethanethiol, 29.1 g (0.469 mole) was then added rapidly dropwise. The reaction mixture was allowed to come to room temperature and was stirred over the weekend at room temperature. The reaction mixture was refluxed about 8 hours and stirred overnight at room temperature; the refluxing and stirring were repeated twice. About 57.3 g of the above-identified product was obtained which was used in Example 6 without further isolation.

EXAMPLE 6

Preparation of

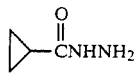

Cyclopropane Carboxylic Acid Hydrazide

To a stirred mixture of 57.3 g (0.440 mole) ethyl cyclopropane carboxythioate (the product of Example 5) in about 25 ml water which was cooled to about −10° C. with a dry ice/acetone bath, 22.0 g (0.440 mole) hydrazine monohydrate was added slowly dropwise (with an exothermic reaction). The mixture first turned orange and then dark green. The reaction mixture was stirred overnight at room temperature, refluxed about 8 hours, and then stirred over the weekend at room temperature. The mixture was extracted with methylene chloride (about 200 ml) and chloroform (about 200 ml) mixed together. The organic phase was dried over magnesium sulfate and then stripped in the hood. The product was then used in Example 7 without further isolation.

EXAMPLE 7

Prepartion of

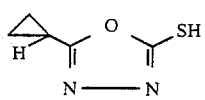

2-Mercapto-5-Cyclopropyl-1,3,4-Oxadiazole

To a stirred mixture of 17.9 g (0.179 mole) cyclopropane carboxylic acid hydrazide (the product of Example 6) in about 75 ml dimethylformamide, 68.0 g (0.894 mole) carbon disulfide was added (and all solids dissolved). The solution turned orange and then green. The reaction mixture was stirred about 1 hour at room temperature, refluxed about 3 hours, and stirred overnight at room temperature. The mixture was added to an ice-water bath to give an oil. The mixture was extracted with methylene chloride. The methylene chloride fraction was dried over magnesium sulfate and stripped. Chromatography on silica gel, eluting with methylene chloride, gave the above-identified product as a solid, melting point 76°–78° C.

Elemental analysis for $C_5H_6N_2OS$ showed: calculated %C 42.23%, %H 4.24, and %N 19.71; found %C 42.47, %H 4.39, and %N 20.05.

EXAMPLE 8

Preparation of

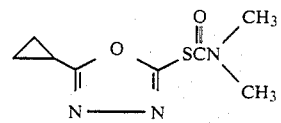

S-(N,N-Dimethylcarbamoyl)-2-Thio-5-Cyclopropyl-1,3,4-Oxadiazole

To a stirred solution of 8.0 g (0.056 mole) 2-mercapto-5-cyclopropyl-1,3,4-oxadiazole (the product of Example 7) is about 200 ml dimethoxyethane which was cooled to about −10° C. in a dry ice/acetone bath, 2.7 g of 50% sodium hydride (0.056 mole) was added slowly (in a very vigorous exothermic reaction). The reaction mixture was stirred about 3 hours at ambient temperature. The mixture was then cooled to about −30° C. with a dry ice/acetone bath, and 44.3 g of 12.5% phosgene (0.056 mole) were added. The resulting mixture was stirred about 12 hours at about 25° C. The reaction mixture was cooled to about 0° C. with a dry ice/acetone bath and 5.05 g (0.0112 mole) anhydrous dimethylamine were added. The resulting mixture was stirred overnight at about 25° C. The mixture was washed with water, extracted with methylene chloride, dried over magnesium chloride and stripped. Chromatography on silica gel, eluting with ether, gave the product as a yellow oil.

Elemental analysis for $C_8H_{11}N_3O_2S$ showed: calculated %C 45.06%, %H 5.20, and %N 19.70; found %C 45.24, %H 5.26, and %N 18.34.

EXAMPLE 9

Preparation of

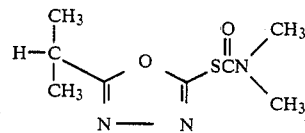

S-(N,N-Dimethylcarbamoyl)-2-Thio-5-Isopropyl-1,3,4-Oxadiazole

To a stirred solution of 13.0 g (0.090 mole) 2-mercapto-5-isopropyl-1,3,4-oxadiazole in about 250 ml dimethoxyethane which had been cooled to about −40° C. with a dry ice/acetone bath, 4.3 g of 50% sodium hydride (0.090 mole) was added slowly (in a vigorous exothermic reaction). The reaction mixture was stirred about 1 hour and cooled as before; then 9.6 g (0.09 mole) N,N-dimethylcarbamoyl chloride was added slowly dropwise. The reaction mixture was stirred overnight at room temperature, refluxed about 4 hours, and stirred overnight at room temperature. The mixture was washed with about 50 ml water and extracted with methylene chloride. The organic phase was dried over magnesium sulfate and stripped. Chromatography on silica gel, eluting with methylene chloride, gave the product as an amber oil.

Elemental analysis for $C_8H_{13}N_3O_2S$ showed: calculated %C 44.63%, %H 6.09, and %N 19.52; found %C 46.52, %H 6.51, and %N 20.45.

Compounds made in accordance with Examples 1 to 9 are shown in Table I.

In addition, by following the procedures described in Examples 1 to 9 using the appropriate starting materials, the following compounds are made:

S-(N,N-dimethylcarbamoyl)-2-thio-5-methoxymethyl-1,3,4-oxadiazole; and

S-(N,N-dimethylcarbamoyl)-2-thio-5-(2-methylthio-isopropyl)-1,3,4-oxadiazole.

EXAMPLE A

Aphid Control

The compounds of the invention were tested for their insecticidal activity against Cotton Aphids (*Aphis gossypii* Glover). An acetone solution of the candidate toxicant containing a small amount of nonionic emulsifier was diluted with water to 40 ppm. Cucumber leaves infested with the Cotton Aphids were dipped in the toxicant solution. Mortality readings were taken after 24 hours. The results are tabulated in Table II in terms of percent control.

EXAMPLE B

Aphid Systemic Evaluation

This procedure is used to assess the ability of a candidate insecticide to be absorbed through the plant root system and translocate to the foliage.

Two cucumber plants planted in a 4-inch fiber pot with a soil surface area of 80 cm² are used. Forty ml of an 80-ppm solution of the candidate insecticide is poured around the plants in each pot. (This corresponds to 40 $\gamma$/cm² of actual toxicant.) The plants are maintained throughout in a greenhouse at 75°–85° F. Forty-eight hours after the drenching, the treated plants are infested with aphids by placing well-colonized leaves over the treated leaves so as to allow the aphids to migrate easily from the inoculated leaf to the treated leaf. Three days after infestation, mortality readings were taken. The results are tabulated in Table II in terms of percent control.

EXAMPLE C

Mite Adult

Two-spotted Mite (*Tetranychus urticae*): An acetone solution of the candidate toxicant containing a small amount of nonionic emulsifier was diluted with water to 40 ppm. Lima bean leaves which were infested with mites were dipped in the toxicant solution. Mortality readings were taken after 24 hours. The results are tabulated in Table II in terms of percent control.

EXAMPLE D

Mite Egg Control

Compounds of this invention were tested for their ovicidal activity against eggs of the two-spotted spider mite (*Tetranychus urticae*). An acetone solution of the test toxicant containing a small amount of nonionic emulsifier was diluted with water to give a concentration of 40 ppm. Two days before testing, 2-week-old lima bean plants were infested with spider mites. Two days after infestation, leaves from the infested plants were dipped in the toxicant solution, placed in a petri dish with filter paper and allowed to dry in the open dish at room temperature. The treated leaves were then held in covered dishes at about 31° C. to 33° C. for seven days. On the eighth day, egg mortality readings were taken. The results, expressed as percent control, are tabulated in Table II.

EXAMPLE E

Housefly

Housefly (*Musca domestica* L.): A 500-ppm acetone solution of the candidate toxicant was placed in a microsprayer (atomizer). A random mixture of anesthetized male and female flies were placed in a contaiiner and 55 mg of the above-described acetone solution was sprayed on them. A lid was placed on the container. A mortality reading was made after 24 hours. The results are tabulated in Table II in terms of percent control.

EXAMPLE F

American Cockroach

American Cockroach (*Periplaneta americana* L.): A 500-ppm acetone solution of the candidate toxicant was placed in a microsprayer (atomizer). A random mixture of anesthetized male and female roaches was placed in a container and 55 mg of the above-described acetone solution was sprayed on them. A lid was placed on the container. A mortality reading was made after 24 hours. The results are tabulated in Table II in terms of percent control.

EXAMPLE G

Alfalfa Weevil

Alfalfa Weevil (*H. burnneipennis* Boheman): A 500-ppm acetone solution of the candidate toxicant was placed in a microsprayer (atomizer). A random mixture of anesthetized male and female flies was placed in a container and 55 mg of the above-described acetone solution was sprayed on them. A lid was placed on the container. A mortality reading was made after 24 hours. The results are tabulated in Table II in terms of percent control.

EXAMPLE H

Cabbage Looper Control

The compounds of the invention were tested for their insecticidal activity against Cabbage Looper (*Trichoplusia ni*). An acetone solution of the candidate toxicant containing a small amount of nonionic emulsifier was diluted with water to 500 ppm. Excised cucumber leaves were dipped in the toxicant solution and allowed to dry. They were then infested with Cabbage Looper larvae. Mortality readings were taken after 24 hours. The results are tabulated in Table II in terms of percent control.

TABLE I

Compounds of the Formula:

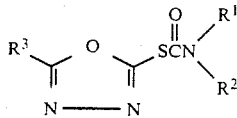

| Compound No. | R¹ | R² | R³ | Physical State | ELEMENTAL ANALYSIS | | | | | |
|---|---|---|---|---|---|---|---|---|---|---|
| | | | | | % Carbon | | % Hydrogen | | % Nitrogen | |
| | | | | | Calc. | Found | Calc. | Found | Calc. | Found |
| 1 30287 | $CH_3$ | $CH_3$ | ⟨cyclopropyl⟩ H | Yellow Oil | 45.06 | 45.24 | 5.20 | 5.26 | 19.70 | 18.34 |
| 2 30288 | $CH_3$ | $CH_3$ | $-C(CH_3)_3$ | Yellow Oil | 47.16 | 47.15 | 6.59 | 6.66 | 18.33 | 18.39 |
| 3 30572 | $CH_3$ | $CH_3$ | $-CH(CH_3)_2$ | Amber Oil | 44.63 | 46.52 | 6.09 | 6.51 | 19.52 | 20.45 |

TABLE II

| Compound No. | A | AS | MA | ME | HF | AR | AW | CL |
|---|---|---|---|---|---|---|---|---|
| 1 30287 | 100 | 100 | 0 | — | 70 | 100 | 10 | 0 |
| 2 30288 | 100 | 100 | 0 | 0 | 100 | 100 | 100 | 100 |
| 3 30572 | 99 | 100 | 0 | 0 | 0 | 99 | 0 | 50 |

A = Aphid
AS = Aphid Systemic
MA = Mite Adult
ME = Mite Egg
HF = Housefly
AR = American Cockroach
AW = Alfalfa Weevil
CL = Cabbage Looper

What is claimed is:

1. A compound the formula:

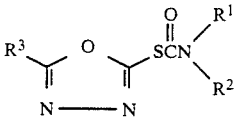

wherein R¹ and R² are independently lower alkyl having from 1 to 4 carbon atoms; and R³ is lower cycloalkyl having from 3 to 6 carbon atoms optionally substituted with methyl or ethyl, lower alkoxyalkyl having up to a total of 8 carbon atoms or lower alkylthioalkyl having up to a total of 8 carbon atoms.

2. A compound according to claim 1 wherein R³ is lower cycloalkyl having from 3 to 6 carbon atoms optionally substituted with methyl or ethyl.

3. A compound according to claim 2 wherein R¹ and R² are methyl.

4. A compound according to claim 3 wherein R³ is cyclopropyl.

5. A method for killing insects which comprises contacting said insects or their habitat with an insecticidally effective amount of the compound of the formula defined in claim 1.

6. A method for killing insects which comprises contacting said insects or their habitat with an insecticidally effective amount of the compound of the formula defined in claim 2.

7. A method for killing insects which comprises contacting said insects or their habitat with an insecticidally effective amount of the compound of the formula defined in claim 3.

8. A method for killing insects which comprises contacting said insects or their habitat with an insecticidally effective amount of the compound of the formula defined in claim 4.

9. An insecticidal composition comprising a biologically inert carrier and an insecticidally effective amount of a compound of the formula defined in claim 1.

10. An insecticidal composition comprising biologically inert carrier and an insecticidally effective amount of a compound of the formula defined in claim 2.

11. An insecticidal composition comprising a biologically inert carrier and an insecticidally effective amount of a compound of the formula defined in claim 3.

12. An insecticidal composition comprising a biologically inert carrier and an insecticidally effective amount of a compound of the formula defined in claim 4.

* * * * *